United States Patent [19]

Luk

[11] 4,446,069

[45] May 1, 1984

[54] PROCESS FOR THE PREPARATION OF β-LACTAM ANTIBIOTICS

[75] Inventor: Kong Luk, Horley, England

[73] Assignee: Beecham Group Limited of Beecham House, Brentford, England

[21] Appl. No.: 269,897

[22] Filed: Jun. 3, 1981

[30] Foreign Application Priority Data

Jun. 11, 1980 [GB] United Kingdom ............... 8019073

[51] Int. Cl.$^3$ .................. C07D 499/00; C07D 501/04
[52] U.S. Cl. ........................ 260/245.2 R; 260/245.3; 260/239.1; 260/245.2 T; 424/270; 424/271
[58] Field of Search .................................. 544/26, 27; 260/245.2 R, 245.3, 245.2 T, 239.1; 546/21; 424/270

[56] References Cited

U.S. PATENT DOCUMENTS 4,255,332 3/1981 Davies .............................. 260/245.3
4,258,050 3/1981 Harbridge ....................... 260/245.3
4,293,555 10/1981 Christensen et al. ............. 260/245.3

FOREIGN PATENT DOCUMENTS 862764 1/1977 Belgium .

Primary Examiner—Nicholas S. Rizzo
Attorney, Agent, or Firm—Hopgood, Calimafde, Kalil, Blaustein & Judlowe

[57] ABSTRACT

The present invention provides a process for the preparation of a fused bicyclic β-lactam containing compound having an optionally salified free carboxylic acid group which process comprises the reaction of an ester of the formula (I):

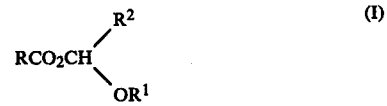

with halide ion; wherein R is the residue of the fused bicyclic β-lactam containing compound, $R^1$ is an alkyl group of 1-6 carbon atoms optionally substituted by an alkoxy group of 1-4 carbon atoms or is an optionally substituted phenyl group or an alkyl group of 1-4 carbon atoms substituted by an optionally substituted phenyl group; and $R^2$ is a hydrogen atom or an alkyl group of 1-4 carbon atoms or is joined to $R^2$ to form part of a 5- or 6- membered carbocyclic or heterocyclic ring.

20 Claims, No Drawings

PROCESS FOR THE PREPARATION OF β-LACTAM ANTIBIOTICS

This invention relates to a process for the removal of an alkoxymethyl esterifying group from a bicyclic β-lactam compound.

Although the use of alkoxymethyl esters of bicyclic β-lactam compounds has frequently been mentioned (eg U.S. Pat. Nos. 4,078,067; 4,051,132; 4,110,165; 4,061,649; 4,076,826 and 3,925,363), there has been very little disclosure concerning methods for ester cleavage thereof. Jackson et al (J. Chem. Soc. Perkin I 1972 page 895) report that methoxymethyl 6β-phthalimidopenicillanate may be hydrolysed to the corresponding free acid using concentrated aqueous hydrochloric acid in acetone. Jansen et al (J. Chem. Soc. 1965 page 2127) report that methoxymethyl benzylpenicillanate has an acid—catalysed mode of hydrolysis. Our own earlier application Belgian Pat. No. 862 764 describes the removal of alkoxymethyl esters of a very small class of compounds by mild base hydrolysis at pH 8-9. We have now found that cleavage of alkoxymethyl esters with halide ions under neutral conditions affords high yields of the corresponding free acids. This method is of particular value in the field of β-lactam compounds which are of value as antibiotics.

Accordingly the present invention provides a process for the preparation of a fused bicyclic β-lactam containing compound having an optionally salified free carboxylic acid group which process comprises the reaction of an ester of the formula (I):

with halide ion; wherein R is the residue of the fused bicyclic β-lactam containing compound, $R^1$ is an alkyl group of 1-6 carbon atoms optionally substituted by an alkoxy group of 1-4 carbon atoms or is an optionally substituted phenyl group or an alkyl group of 1-4 carbon atoms substituted by an optionally substituted phenyl group; and $R^2$ is a hydrogen atom or an alkyl group of 1-4 carbon atoms or is joined to $R^2$ to form part of a 5- or 6- membered carbocyclic or heterocyclic ring.

The term "optionally substituted phenyl" means a phenyl group unsubstituted or substituted by one or more fluorine, chlorine or bromine atoms or $C_{1-4}$ alkoxy, $C_{1-4}$ alkoxycarbonyl, nitro or similar inert groups. Substituted groups are most suitably mono-substituted or di-substituted, preferably mono-substituted.

Suitable solvents include polar solvents, for example dimethylformamide, dimethoxyethane, dioxan, tetrahydrofuran, dimethoxydiethyl ether, dimethylsulphoxide, acetone, methanol, ethanol, propanol, butanol, amyl alcohol, hexanol, acetonitrile and mixtures of such solvents optionally in the presence of moisture.

Suitably the halide ion is bromide or iodide ion. The counter-ion may be organic or inorganic. Suitable counter-ions include alkali metal ions such as lithium, sodium and potassium; alkaline earth metal ions such as caesium, calcium and magnesium; and ammonium and substituted ammonium ions such as $NR_aR_bR_cR_d$ wherein $R_a$, $R_b$, $R_c$ and $R_d$ are independently hydrogen, $C_{1-6}$ alkyl or optionally substituted phenyl ($C_{1-6}$) alkyl, for example trimethylammonium and tetramethylammonium.

A preferred source of halide ions is lithium bromide or potassium iodide.

Preferably in the process of this invention the counter-ion is pharmaceutically acceptable so that a pharmaceutically acceptable salt is formed, but if a non-pharmaceutically acceptable salt is used then the product may be converted to a pharmaceutically acceptable salt in conventional manner, for example ion-exchange.

The process of this invention is preferably performed at a non-extreme temperature, for example −30° C. to +60° C., more suitably −10° C. to +40° C. and most conveniently at ambient temperature.

Suitably $R^1$ is a methyl, ethyl, propyl, phenyl, p-chlorophenyl, p-methoxyphenyl, p-nitrophenyl benzyl or p-chlorobenzyl group.

Suitably $R^2$ is a hydrogen atom or a methyl group or is joined to $R^1$ to form the residue of a tetrahydrofuranyl or tetrahydropyranyl ring.

Most suitably $R^2$ is a hydrogen atom and $R^1$ is an alkyl group of 1-6 carbon atoms or an optionally substituted phenyl group or an alkyl group of 1-4 carbon atoms substituted by an optionally substituted phenyl group.

Preferably $R^2$ is a hydrogen atom and $R^1$ is selected from methyl, ethyl, propyl, phenyl or benzyl.

A particularly preferred group $CO_2CHR^2OR^1$ is the methoxymethyl ester, i.e. $R^1$ is methyl and $R^2$ is hydrogen.

Suitably R is the residue of a penicillin, penicillin derivative, carbapenem, cephalosporin, oxacephem, penam or clavulanate derivative, wherein the carboxylic acid group is attached to the 2-position, i.e. adjacent the nitrogen atom of the β-lactam ring. A variety of such compounds are well known as antibacterial agents in the literature.

More suitably the group R is of the formula (II):

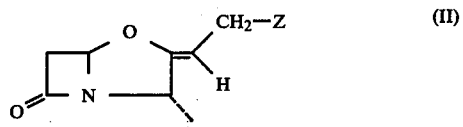

wherein Z is selected from hydrogen, hydroxyl, substituted hydroxy for example etherified or esterified hydroxy, mercapto, substituted mercapto for example etherified or esterified mercapto, amino, mono- or dihydrocarbylsubstituted amino, or mono- or di- acylamino.

Most suitably Z is selected from hydrogen, hydroxy, hydroxy substituted by optionally substituted $C_{1-6}$ alkyl, aryl $C_{1-6}$ alkyl such as optionally substituted phenyl ($C_{1-6}$) alkyl, or groups of the sub-formula $CHR^2OR^1$ as hereinbefore defined for example $C_{1-6}$ alkoxy methyl, $C_{1-6}$ alkyl amino, di- $C_{1-6}$ alkylamino or optionally substituted phenyl ($C_{1-6}$) alkyl amino.

In particular it is preferred that Z is methoxymethoxy.

Particular compounds which may be prepared by this process include:

(i) Sodium 9-O-methoxymethylclavulanate
(ii) Sodium clavulanate, and
(iii) Sodium 6β-(nitrobenzenesulphonyloxy)penicillanate.

The following Examples serve to illustrate the invention.

EXAMPLE 1

Preparation of sodium 9-O-methoxymethylclavulanate

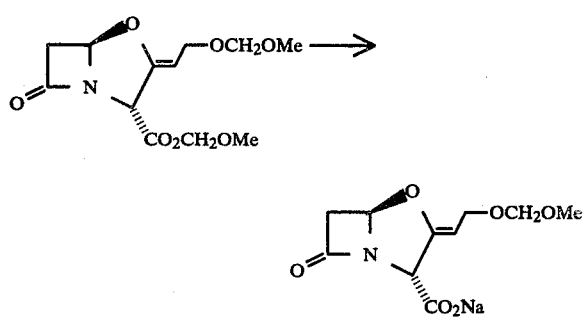

A mixture of methoxymethyl 9-O-methoxymethyl-clavulanate (0.55 g), lithium bromide (0.6 g), and N,N-dimethylformamide (5 ml) was stirred at room temperature overnight. The mixture was then poured into ice-water (50 ml) which xas saturated with sodium chloride and extracted with ethyl acetate (50 ml). The organic extract was dried with magnesium sulphate and filtered. Sodium ethylhexanoate in methyl isobutyl ketone (2 M, 0.9 ml) was then added to the filtrate and the mixture concentrated to 5 ml. Dilution with diethyl ether (250 ml) gave sodium 9-O-methoxymethylclavulanate as a precipitate (0.4 g).

EXAMPLE 2

Preparation of sodium clavulanate

Lithium bromide (0.1 g) was added to a solution of methoxymethyl clavulanate (0.1 g) in N,N-dimethylformamide (3 ml) at 0° and the mixture was stirred at room temperature overnight. This was poured into water-ethyl acetate (1:1, 20 ml) which was then saturated with sodium chloride. The ethyl acetate layer was separated and dried over anhydrous sodium sulphate. This was then filtered and extracted with water (10 ml) at pH 7.5, maintained by the addition of aqueous sodium hydroxide. The aqueous extract was then evaporated to dryness to afford sodium clavulanate (0.05 g), identical to an authentic sample by $^1$H n.m.r. comparison.

EXAMPLE 3

Preparation of sodium 6β-(p-nitrobenzenesulphonyloxy)penicillanate

To a solution of methoxymethyl 6β-(p-nitrobenzenesulphonyloxy)penicillanate (0.18 g) in dimethylformamide was added lithium bromide (0.3 g). The solution was stirred overnight, then poured onto iced water and extracted with ethyl acetate (3×30 ml). The ethyl acetate layer was separated, washed with water and dried over anhydrous magnesium sulphate. The solution was then reduced to a small volume (5 ml), water (5 ml) was added and the pH was adjusted to 7.5 with sodium hydroxide. The aqueous layer was separated and the water removed in vacuo to yield a pale yellow glass (0.13 g) which on silica gel chromatography using butanol:ethanol:water (4:1:1) as eluant yielded sodium 6β-(p-nitrobenzenesulphonyloxy)-penicillanate (0.07 g) as a pale yellow glass, $\nu_{max}$ (KBr) 1780, 1605, 1535, 1350, 1190 cm$^{-1}$; δ(D$_2$O) 8.34 (2H, d, J=9 Hz, Ar$\underline{H}$), 8.05 (2H, d, J=9 Hz, At$\underline{H}$), 5.88 (1H, d, J=4 Hz, $\underline{H}$—C$_6$), 5.43 (1H, d, J=4 Hz, $\underline{H}$—C$_5$), 4.16 (1H, s, $\underline{H}$—C$_3$), 1.43 (3H, s, gem C$\underline{H}_3$), 1.35 (3H, s, gem CH$_3$).

I claim:

1. A process for the preparation of a fused bicyclic β-lactam containing compound having an optionally salified free carboxylic acid group, which consists essentially of reacting an ester of the formula (I):

wherein R is a fused bicyclic β-lactam selected from the group consisting of a penicillin, penicillin derivative, carbapenem, cephalosporin, oxacephem, penam, and clavulanate derivative, wherein the carboxylic acid group is attached to the position adjacent to the nitrogen of the β-lactam ring, within the ring which is fused to the β-lactam ring; R$^1$ is alkyl of 1-6 carbon atoms unsubstituted or substituted by alkoxy of 1-4 carbon atoms; phenyl unsubstituted or substituted by one or more fluoro, chloro, bromo, alkoxy of 1 to 4 carbon atoms, alkoxycarbonyl of 1 to 4 carbon atoms or nitro or alkyl group of 1-4 carbon atoms substituted by phenyl unsubstituted or substituted by one or more fluoro, chloro, bromo, alkoxy of 1 to 4 carbon atoms, alkoxycarbonyl of 1 to 4 carbon atoms or nitro; and R$^2$ is hydrogen or alkyl of 1-4 carbon atoms or is joined to R$^1$ to form a tetrahydrofuranyl or tetrahydropyranyl ring, with a halide ion under neutral conditions.

2. A process according to claim 1 wherein the halide ion is bromide or iodide ion.

3. A process according to claim 1 wherein the counter-ion is an alkali metal ion or an alkaline earth metal ion.

4. A process according to claim 3 wherein the source of halide ions is lithium bromide or potassium iodide.

5. A process according to claim 1 wherein the reaction temperature is −10° C. to +40° C.

6. A process according to claim 1 wherein R$^2$ is hydrogen.

7. A process according to claim 1 wherein R$^1$ is methyl, ethyl, propyl, phenyl or benzyl.

8. A process according to claim 1 wherein the group CHR$^2$OR$^1$ is methoxymethyl.

9. A process according to claim 1 wherein R is of the formula (II):

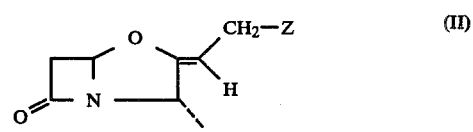

wherein Z is a hydrogen, hydroxy, hydroxy substituted by C$_{1-6}$ alkyl, aryl C$_{1-6}$ alkyl, C$_{1-6}$ alkylamino, di-C$_{1-6}$ alkylamino or phenyl (C$_{1-6}$) alkylamino; mercapto, etherified mercapto, or esterified mercapto; amino, monohydrocarbyl amino, or di-hydrocarbyl amino or mono-acylamino or di-acylamino.

10. A process according to claim 1 for the preparation of a pharmaceutically acceptable salt of 9-O-methoxymethylclavulanic acid, clavulanic acid or 6β-nitrobenzenesulphonyloxypenicillanic acid wherein the counter-ion is pharmaceutically acceptable.

11. A process according to claim 1 wherein $R^1$ is methyl, ethyl, propyl, phenyl, p-chlorophenyl, p-methoxyphenyl, p-nitrophenyl, benzyl or p-chlorobenzyl.

12. A process according to claim 1 wherein the phenyl group when it is substituted is mono- or di-substituted.

13. A process according to claim 12 wherein the phenyl substitution is mono-substitution.

14. A process according to claim 1 wherein the counter-ion is a pharmaceutically acceptable one.

15. A process according to claim 1 wherein $R^1$ is methyl and $R^2$ is hydrogen.

16. A process according to claim 9 wherein Z is hydrogen, hydroxy unsubstituted or substituted by alkyl of 1 to 6 carbon atoms or phenyl alkyl of 1 to 6 carbon atoms in the alkyl moiety, alkoxymethyl of 1 to 6 carbon atoms in the alkoxy moiety and alkylamino of 1 to 6 carbon atoms in the alkyl moiety, di-alkylamino of 1 to 6 carbon atoms in each alkyl moiety or phenyl alkylamino of 1 to 6 carbon atoms in the alkyl moiety.

17. A process according to claim 9 wherein Z is methoxymethyl.

18. A process for the preparation of sodium 9-O-methoxymethylclavulanate which comprises reacting a mixture of methoxymethyl 9-O-methoxyclavulanate, lithium bromide and N,N-dimethylformamide under neutral conditions, pouring the mixture into an aqueous solution saturated with sodium chloride, extracting with ethyl acetate, drying the organic extract, filtering, adding sodium ethylhexanoate in methyl isobutyl ketone to the filtrate, concentrating the mixture, diluting the mixture with diethyl ether and recovering sodium 9-O-methoxymethylclavulanate.

19. A process according to claim 1 for the production of sodium clavulanate which comprises adding lithium bromide to a solution of methoxymethylclavulanate in N,N-dimethylformamide under neutral conditions, pouring the mixture into an aqueous ethyl acetate mixture which is then saturated with sodium chloride, separating the ethyl acetate layer, drying the layer, filtering and extracting the layer and evaporating the aqueous extract to dryness to obtain sodium clavulanate.

20. A process according to claim 1 for the production of sodium 6β-(p-nitrobenzenesulphonyloxy)penicillanate which comprises adding lithium bromide to a solution of methoxymethyl 6β-(p-nitrobenzenesulphonyloxy)penicillanate and dimethylformamide under neutral conditions, pouring the solution into an aqueous solution, extracting the solution with ethyl acetate, separating the ethyl acetate layer, washing the same, drying the same, reducing the volume and adjusting the pH to 7.5, separating the aqueous layer and removing the water to yield sodium 6β-(p-nitrobenzenesuplphonyloxy)penicillanate.

* * * * *